United States Patent [19]

Zofchak

[11] Patent Number: 4,548,810

[45] Date of Patent: Oct. 22, 1985

[54] METHOD OF LUBRICATING THE SKIN

[76] Inventor: Albert Zofchak, 6 Gulfstream Blvd., Matawan, N.J. 07749

[21] Appl. No.: 261,869

[22] Filed: May 8, 1981

Related U.S. Application Data

[63] Continuation of Ser. No. 35,866, May 3, 1979, abandoned.

[51] Int. Cl.$^4$ .......... A61K 7/06; A61K 7/15; A61K 7/42
[52] U.S. Cl. .......... 424/59; 252/106; 252/107; 260/404; 260/404.5; 260/501.1; 260/501.17; 424/47; 424/60; 424/70; 424/73; 568/814; 514/784; 514/844
[58] Field of Search .......... 424/70, 73, 59, 60; 260/501.1, 501.17, 404, 404.5

[56] References Cited

U.S. PATENT DOCUMENTS

| | | | |
|---|---|---|---|
| 2,089,212 | 8/1937 | Kritchersky | 424/317 |
| 2,228,986 | 1/1941 | De Groote et al. | 252/356 |
| 2,307,775 | 1/1943 | Flenner et al. | 424/325 |
| 2,484,146 | 10/1949 | Barber | 424/325 |
| 2,514,954 | 7/1950 | Johnson et al. | 260/404.5 PA |
| 2,587,546 | 2/1952 | Matuszak | 260/404.5 PA |
| 2,663,648 | 12/1953 | Jelling | 260/404.5 PA |
| 2,664,429 | 12/1953 | Goebel | 260/407 |
| 2,681,354 | 6/1954 | Kelley et al. | 260/404.5 EO |
| 2,736,658 | 2/1956 | Pfohl et al. | 260/404.5 PA |
| 2,828,323 | 3/1958 | De Groote et al. | 260/404.5 EO |
| 3,734,859 | 5/1973 | Ward | 252/117 |
| 3,822,312 | 7/1974 | Sato et al. | 252/527 |

*Primary Examiner*—Dale R. Ore
*Attorney, Agent, or Firm*—Francis W. Young; Louis A. Morris

[57] ABSTRACT

Compositions obtained by reacting a tertiary amine having at least one long-chain group with a long-chain acid are disclosed. The compositions are useful in non-irritating skin or hair-contacting compositions, such as shaving creams, hair conditioners, skin conditioners, and aftershave. The compositions are also useful in non-irritating soap and dishwashing compositions. The compositions provide a combination of properties such as long-lasting slip, lubrication, emolliency, softening, and conditioning.

12 Claims, No Drawings

METHOD OF LUBRICATING THE SKIN

This is a continuation of application Ser. No. 035,866, filed May 3, 1979, now abandoned.

BACKGROUND OF THE INVENTION

This invention relates to the cosmetic, toiletry, hand soap, detergent and fabric softening area. More particularly, this invention relates to additives for use in cosmetic, toiletry hand soap, detergent and fabric softening formulations.

SUMMARY OF THE INVENTION

It has been surprisingly discovered that tertiary amine salts of the formula

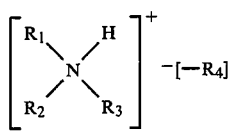

wherein $R_1$ is selected from the group consisting of saturated and unsaturated aliphatic groups containing from about 8 to about 22 carbon atoms, $$\overset{O}{\underset{\|}{RCNHCH_2CH_2CH_2}}-, \overset{O}{\underset{\|}{RCNHCH_2CH_2}}-,$$

$RN(CH_3)CH_2CH_2CH_2-$, $RN(CH_2CH_2O)_{1-5}HCH_2CH_2CH_2-$, $$\overset{O}{\underset{\|}{RCOCH_2CH_2}}-, CH_3O[CH_2CH(CH_3)O]_{1-5}CH_2CH_2CH_2-,$$

$H[O(CH_3)CHCH_2]_{3-8}$, $H[O(CH_3)CHCH_3]_{3-8}OCH_2CH_2-$, $RCHOHCH_2-$, $ROCH_2CH_2CH_2-$, $$\underset{|}{\overset{R_5}{(HOCHCH_2)_2NCH_2CH_2CH_2}}-,$$

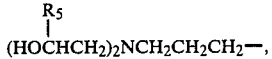

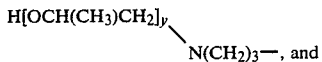

$R_3$ is selected from the group consisting of aliphatic groups containing from about one to about two carbon atoms, $H[O(CH_3)CHCH_2]_{1-15}-$ and $H(OCH_2CH_2)_{1-15}-$, $R_2$ is selected from the group consisting of saturated and unsaturated aliphatic groups containing from about 8 to about 22 carbon atoms, $$\overset{O}{\underset{\|}{RCNHCH_2CH_2CH_2}}-, \overset{O}{\underset{\|}{RC\phi NHCH_2CH_2}}-,$$

$R(OCH_2CH_2CH_2)_zN(CH_3)CH_2CH_2CH_2-$,
$R(OCH_2CH_2CH_2)_zN(CH_2CH_2O)_{1-5}HCH_2CH_2CH_2-$, $$\overset{O}{\underset{\|}{RCOCH_2CH_2}}-,$$

$CH_3O[CH_2CH(CH_3)O]_{1-5}CH_2CH_2CH_2-$,
$H[O(CH_3)CHCH_2]_{3-8}$, $H[O(CH_3)CHCH_2]_{3-8}OCH_2C-H_2-$, $RCHOHCH_2-$, $ROCH_2CH_2CH_2-$, aliphatic groups containing from one to about two carbon atoms and $H[O(CH_3)CHCH_2]_{1-15}-H(OCH_2CH_2)_{1-15}-$, and $R_4$ is selected from the group consisting of $$\underset{\|}{\overset{O}{R-C-O}}-,$$

$RCH=CH_2SO_3-$, $RCONHCH(CH_3)CO_2-$, $ROSO_3-$, $RC_6H_5SO_3-$, $RO[CH_2CH_2O]_{1-10}CH_2CO_2-$, $RNHCOCH=CHCO_2-$, isostearic acid residue, ricinoleic acid residue, hydroxystearic acid residue, phenylstearic acid residue and residues of dibasic acids containing from about 6 to about 36 carbon atoms, wherein in all instances R represents a saturated or unsaturated aliphatic group containing from about 8 to about 18 carbon atoms, $R_5$ is an aliphatic group containing from about 8 to about 22 carbon atoms, x and y are integers from 1 to 9, the sum of $x+y$ is an integer from 2 to 10, and z is 0 or 1 are useful as additives in cosmetic, toiletry soap, detergent, and fabric softening formulations.

The foregoing is especially surprising in view of the fact that tertiary amines are in general considered to be primary skin irritants. The tertiary amine salts of the present invention, however, when utilized at the recommended levels, are not primary skin irritants. As far as is presently known, the only somewhat similar types of salt which have been suggested in the art are the propionate, lactate, and tartrate salts of a tertiary amine of the formula $$\underset{\|}{\overset{O}{RCNH(CH_2)_3N(CH_3)_2}}$$

which have been suggested for use in applications such as hair shampoos. As far as is known such usage has never been developed commercially.

As the compositions useful in the present invention may be derived from the reaction of less than stoichiometric ratios of the tertiary amine and the acid, the compositions may be described as the product formed by reacting a tertiary amine of the formula:

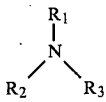

with an acid of the formula:

H—R$_4$ wherein $R_1$, $R_2$, $R_3$, and $R_4$ have the meanings defined above, in a molar ratio of amine:acid from about 0.3:1 to about 3.3:1.

The composition which is useful in providing the desired characteristics may be described as the product formed by mixing water, a tertiary amine of the formula:

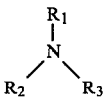

and an acid of the formula:

wherein $R_1$, $R_2$, $R_3$, and $R_4$ have the meanings defined above, in a molar ratio of amine:acid from about 0.3:1 to about 3.3:1.

The present invention thus provides non-irritating skin or hair-contacting formulations comprising a tertiary amine salt as defined above. The non-irritating skin or hair contacting formulations may also comprise the reaction product formed from the tertiary amine and the acid as described hereinabove, and/or may comprise the product formed by mixing water with the tertiary amine and the acid.

DETAILED DESCRIPTION OF THE PREFERRED EMBODIMENTS

As indicated, the present invention provides unique additives which are useful in many application areas. The compositions of the present invention may be used in a wide array of applications and numerous skin and hair preparations in the cosmetic and toiletry industry. For example, the compositions may be used in after-shave lotion to provide long-lasting emolliency, in pre-electric shave lotion for reduction of friction, in shaving creams for lubrication and emollient after feel, in bath oil for emolliency and softening of the skin, in after-bath products, in hair preparations as a sheening agent, in sunscreen preparations as a skin conditioner or potential substantive agent, in hair formulations as a softener and conditioner, and skin and hand preparations as an emollient, lubricant, or protective film former, in shampoo as a conditioner and the like. The foregoing are merely illustrative of the potential applications of the compositions of the present invention in the area of skin and hair-contacting agents, and they are not meant as limitation on the scope of the present invention.

The use of salts and compositions of the present invention and the foregoing formulations utilize the physical attributes of the present salts and compositions with respect to slip, lubrication, conditioning, emolliency, and softening properties. Many of the salts and compositions of the present invention also possess other physical characteristics which are desirable, such as dispersability in water and broad solubility or dispersability in mineral oil, amides, esters, alcohols, glycols, natural oils, and the like.

The salts and compositions of the present invention may be prepared by any of the known methods of preparing amine salts of fatty acids. A simple method is to simply mix the fatty acid and the amine. If stoichiometric ratios are utilized, the product will be the simple amine salt formed from the tertiary amine and the acid or, in the presence of water its hydrolysate. As indicated, it is possible to prepare useful products employing molar ratios of amine:acid from about 0.3:1 to about 3.3:1. Thus, ratios less than 1:1, as from about 0.3:1 to about 0.99:1 may be employed, as well as greater than one, as from about 1.01:1 to about 3.3:1.

If other than stoichiometric ratios are utilized, the product will be the aforementioned amine salt or, in the presence of water, its hydrolysate, in combination with the excess tertiary amine or excess acid. It is believed that the most beneficial results are achieved with the present invention when water is present, possibly resulting in some undefined complexing with water. It is not known whether the reaction product exists as a simple mixture of the tertiary amine salt or hydrolysate with the unreacted tertiary amine or unreacted acid, or in some undefined complex. In any event, it appears that even when other than stoichiometric ratios are employed, the resulting composition is non-irritating at the recommended levels of usage. For sake of simplicity the products of the present invention will simply be referred to by means of their process of manufacture, the reaction of the tertiary amine with the acid, optionally in the presence of water.

Generally, the amount of acid which is utilized is preferably greater when tertiary amines which are highly basic are utilized, and preferably less when tertiary amines having less basic properties are employed. Also, as the strength of the various acids vary considerably, one should understand that with stronger acids it is typically perferred to utilized less acid than when employing a weaker acid.

As indicated, the tertiary amine salts, and/or the reaction products obtained from the tertiary amines and acids, and their hydrolysates may be incorporated into customary shaving compositions, conventional hair and skin-contacting preparations, and the like. Such skin and hair-contacting compositons include compositions such as those described in "Cosmetics Science and Technology", edited by Edward Sagarin, Interscience Publishers, Inc., New York (1972 and 1974).

Likewise, the aforementioned salts and reaction products may be utilized in dishwashing formulations as well as soap formulations, such as soap bars.

When the salts and reaction products of the present invention are utilized in the foregoing manner, incorporation into skin or hair-contacting preparations, dishwashing formulations, or soaps, it is preferable to utilize the salts or reaction products of the present invention in an amount up to about 5%, by weight, of the total formulation. Preferably, an amount about equal to or less than 2% is utilized, such as from about 0.1 to about 2.0%, by weight. Typically, the salt or reaction product will be utilized in an amount of about 1%, by weight, based on the total weight of formulation.

Of the possible tertiary amine salts useful in the practice of the present invention, the following are included: dimethyllaurylamine oleate, dimethyllaurylamine stearate, dimethylpalmitylamine oleate, diethyllaurylamine oleate, dimethylpalmitylamine stearate, polyoxyethylene(15)tallowamine oleate, bis(2-hydroxyethyl)tallowamine oleate, N,N-dimethylcocoamine isostearate, and N,N-dimethyloctadecylamine oleate. Useful fabric conditioning compositions result from a reaction of the defined acids with tertiary amines such as methyldicocoamine and methyldi-hydrogenatedtallowamine.

For use in the area of dandruff control, tertiary amine salts of the defined formula may be reacted with undecylenic acid.

In general, the preferred compositions of the present invention will be derived from tertiary amines of the defined formula wherein $R_1$ is a saturated or unsatu-

EXAMPLE 6

Hand Lotion

|  | Parts |
|---|---|
| Dimethyllaurylamine stearate | 1.5 |
| Mineral oil, light 70/80 | 15.5 |
| Sorbitan oleate | 5.5 |
| Stearyl alcohol | 2.5 |
| Polyethyleneglycol 2000 monostearate | 4.5 |
| Methyl paraben | 0.1 |
| Propyl paraben | 0.04 |
| Deionized water q.s. | 100 |

Hands treated with the lotion are soft, smooth and non-greasy.

EXAMPLE 7

After-shave Lotion

|  | Parts |
|---|---|
| Dimethylpalmitylamine oleate | 3.0 |
| Isopropyl alcohol | 72.0 |
| Glycerol p-amino benzoate | 3.0 |
| Water | 22.0 |
| TOTAL | 100.0 |

Splashing lotion on the face after a shave provides a refreshing feeling and a smooth, soft complexion.

EXAMPLE 8

Skin Cream

|  | Parts |
|---|---|
| Dimethyllaurylamine oleate | 2.0 |
| Diethanolstearamide | 3.0 |
| Stearic acid | 2.0 |
| Light mineral oil | 5.0 |
| Water | 88.0 |
| TOTAL | 100.0 |

The cream provides a soft, velvety talc feel to the skin.

EXAMPLE 9

Hair Dressing

|  | Parts |
|---|---|
| Dimethylpalmitylamine stearate | 3.0 |
| Ucon LB-385 (polyalkyleneglycol polymer) | 97.0 |
| TOTAL | 100.0 |

Treatment of hair with the dressing results in soft hair.

EXAMPLE 10

Liquid Lotion Hand Cleaner

|  | Parts |
|---|---|
| Ethyleneglycolmonostearate | 0.5 |
| Natrosol 250HR | 0.3 |
| Triethanolaminelaurylsulfate (40%) | 14.0 |
| Stepanol WA Paste | 14.0 |
| Ninol 2012 Extra | 2.0 |
| Methylparaben | 0.1 |
| Polysorbate 80 | 2.0 |
| Dimethyllaurylamine oleate | 2.0 |
| Perfume, color, water q.s. | 100 |

EXAMPLE 11

Bar Soap

|  | Parts |
|---|---|
| Dimethyllaurylamine oleate | 2.0 |
| Triethanolaminedodecyl sulfate | 40.0 |
| Coconut oil fatty acids | 10.0 |
| Soap of mixed tallow/coconut oil (80/20) | 43.0 |
| Water | 5.0 |
| TOTAL | 100.0 |

This bar soap exhibits excellent lathering and leaves hands soft and smooth.

The compositions in Examples 12–18 are prepared as described:

EXAMPLE 12

Moisturizing Cream

|  | Parts |
|---|---|
| Phase A |  |
| Veegum (Complex colloidal magnesium aluminum silicate) | 1.50 |
| Water | 72.80 |
| Methyl paraben | 0.10 |
| Glycerine | 4.00 |
| Trithanolamine | 1.00 |
| Phase B |  |
| Dimethyllaurylamine oleate | 1.00 |
| Lanolin oil | 10.00 |
| Stearic Acid, Triple-pressed | 2.00 |
| Isopropyl myristate | 2.00 |
| Glycerol monostearate, S.E., Acid Stable | 3.00 |
| Cetyl alcohol | 2.00 |
| Propyl paraben | 0.05 |
| Perfume | 0.55 |
| TOTAL | 100.00 |

In preparation of Phase A, Veegum is added to water, mixed for ten minutes and heated until the temperature reaches about 50° C. at which time the remaining ingredients of Phase A are added. The mixture is further heated to about 70° C.

Phase B is mixed in a separate container and heated to about 75° C. Phase B is then added to Phase A at about 70° C. After cooling to about 35° C. with slow agitation, the perfume is added.

The cream is especially useful for making dried skin soft and smooth without leaving a greasy feeling.

EXAMPLE 13

Bubble Bath

|  | Parts |
|---|---|
| Dimethyllaurylamine oleate | 2.00 |
| Water | 50.90 |
| Methyl paraben | 0.10 |
| Standapol WAQ Special (sodium lauryl ether sulfate, 50%; low salt content) | 35.00 |
| Foamid L (diethanollauramide) | 5.00 |
| Polyethyleneglycol 6000 distearate | 2.00 |
| Ethyleneglycol monostearate | 2.00 | rated aliphatic group containing from about 8 to about 22 carbon atoms, and $R_2$ and $R_3$ are selected from the group consisting of methyl, ethyl, $H[O(CH_3)CHCH_2]_{1-15}$— and $H(OCH_2CH_2)_{1-15}$—, and $R_4$ is a saturated or unsaturated aliphatic carboxylic acid group containing from about 8 to about 22 carbon atoms. Typically $R_2$ and $R_3$ will be methyl.

In some instances it may be desirable to employ dibasic acids containing from about 6 to about 36 carbon atoms. Exemplary of such acids are the dimer acids from Emery, such as Empol 1016 which has the general formula $HO_2C[C_{34}H_{62}]CO_2H$, Westvaco Diacid 1550 which has the general formula $HO_2C[C_{19}H_{34}]CO_2H$, and the typically available dibasic acids having the formula $HO_2C(CH_2)_bCO_2H$, wherein b is from about 4 to about 20. One may refer to U.S. Pat. No. 2,664,429 and J. C. Cowan, J. Am. Oil Chem. Soc., Vol. 39, p. 534 et seq (1962) which are incorporated herein by reference, with respect to available types of dimer acids. Also one may refer to U.S. Pat. No. 3,734,859, which is also incorporated herein by reference, which indicates that the Westvaco type of dimer acid is a mixture of 5-carboxy-4-hexyl-2-cyclohexene-1-octadecanoic acid and 6-carboxy-4-hexyl-2-cyclohexene-1-octadecanoic acid.

As previously indicated, the useful tertiary amines include diamine structures such as N,N',N'-trimethyl-N'alkylpropanediamine. Thus, if the aforementioned dimer acids are reacted with appropriate diamines, it is possible that the resultant product may be polymeric. Other diamines which may be reacted with dimer acids to possibly produce polymeric products include diamines of the structure

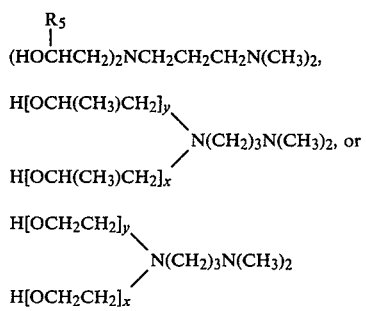

where x and y are integers from 1 to 9 and the sum of x+y is from 2 to about 10, and $R_5$ is an aliphatic group containing from about 8 to about 22 carbon atoms.

The scope of the present invention will be further illustrated by the following non-limiting examples.

EXAMPLE 1

Dimethyllaurylamine Oleate 2,650 grams of dimethyllaurylamine, 4,450 grams of oleic acid, 5 grams of Ionol and 25 grams of hypophosphorous acid are reacted at a temperature not exceeding 125° C. and high vacuum was utilized to remove any volatiles. The resulting product was within the scope of the present invention and this procedure represents the preferred process for making the salts and compositions of the present invention. The Ionol (ditertiarybutyl-para-cresol) and hypophosphorous acid are utilized to retard rancidification and to bleach the reaction product.

EXAMPLE 2

Pre-shave Lotion

|  | Parts |
| --- | --- |
| Dimethyllaurylamine oleate | 0.5 |
| Diisopropyl adipate | 10.0 |
| Ethanol | 60.0 |
| Boric acid | 1.0 |
| Perfume | 0.5 |
| Distilled water | 28.0 |
| TOTAL | 100.0 |

The lotion is applied to the bearded area of the face and allowed to dry before shaving with an electric razor. The result is an even, close shave with no pulling or nicking. The face is smooth and soft to the touch.

EXAMPLE 3

Bath Oil

|  | Parts |
| --- | --- |
| Dimethyllaurylamine oleate | 1 |
| Isopropyl palmitate | 45 |
| Light mineral oil | 45 |
| Sorbitan sesquioleate | 5 |
| Perfume | 4 |
| TOTAL | 100 |

The bath oil provides a silky smooth feel to the skin.

EXAMPLE 4

Aerosol Shaving Cream

|  | Parts |
| --- | --- |
| Dimethyllaurylamine oleate | 1.5 |
| Potassium stearate | 5.0 |
| Sodium stearate | 1.0 |
| Mineral oil | 20.0 |
| Stearic acid | 0.2 |
| Coconut fatty acid | 0.7 |
| Glycerine | 3.0 |
| Polyvinyl pyrrolidene | 0.1 |
| Perfume | 0.5 |
| Water | 58.0 |
| Propellant (dichlorodifluoromethane) | .10.0 |
| TOTAL | 100.0 |

The shaving cream has excellent lathering properties and the shave is smooth and close with minimal razor drag. The facial skin feels soft and velvety after shaving.

EXAMPLE 5

Shampoo

|  | Parts |
| --- | --- |
| Dimethyllaurylamine oleate | 1.0 |
| Sodium lauryl sulfate | 7.0 |
| Diethanollauramide | 3.0 |
| Triethanolamine salt of the monoester of succinic acid and coconut monoethanolamide | 3.0 |
| Water | 86.0 |
| TOTAL | 100.0 |

Lathering and cleansing properties are excellent and the hair is left soft and shining.

| | Parts |
|---|---|
| Perfume | 2.00 |
| Color | 1.00 |
| TOTAL | 100.00 |

Methyl paraben and Standapol WAQ Special are added to water and heated to about 70° C. with agitation until homogeneity is achieved.

In a separate beaker the dimethyl lauryl amine oleate is mixed with Foamid L and the mixture heated until uniform. This mixture is slowly added to the water phase described above.

Polyethyleneglycol 6000 distearate is added and the solution mixed until thoroughly dissolved. Ethyleneglycol monostearate is then added with mixing until dissolved. Finally, the solution is cooled to about 25° C. and perfume and color are added.

EXAMPLE 14

Low pH Conditioning Shampoo

| | Parts |
|---|---|
| Water | 63.45 |
| Standapol A (sodium lauryl ether sulfate, 30%) | 30.00 |
| Foamid LM (lauric/myristic diethanolamide) | 3.00 |
| Dimethyllaurylamine oleate | 1.00 |
| Methyl paraben | 0.20 |
| Citric acid | 0.15 |
| Sodium chloride | 1.00 |
| Perfume | 0.20 |
| Color | 1.00 |
| TOTAL | 100.00 |

Water was heated in a jacketed vessel equipped with a variable speed agitator. Citric acid was added and the solution was heated to about 60° C. at which time all remaining ingredients except sodium chloride and perfume were added. The mixture was heated to about 75° C. and held at that temperature for about 30 minutes.

The mixture was cooled and perfume and sodium chloride were added when the temperature reached about 40° C. The final product was then cooled to about 25° C.

Lathering, cleansing and rinsing properties were excellent even in hard water. After use, it was observed that the hair has good manageability and luster.

EXAMPLE 15

Lotion

| | Parts |
|---|---|
| Phase A | |
| Water | 82.20 |
| Lactic acid 88%, (10% solution) | 1.00 |
| Methyl paraben | 3.00 |
| Glycerine | 3.00 |
| Cellosize QP-300-H (cellulose ether) | 2.00 |
| Phase B | |
| Glycerol monostearate | 3.50 |
| Foamid 0-100 (dimethylaminopropyloleamide) | 0.30 |
| Myristyl myristate | 1.00 |
| 2-Ethylhexyl palmitate | 2.00 |
| Cetyl alcohol | 0.50 |
| Dimethyllaurylamine oleate | 1.00 |
| Propyl paraben | 0.10 |
| Perfume | 0.40 |

| | Parts |
|---|---|
| TOTAL | 100.00 |

Water, lactic acid solution and methyl paraben are mixed and heated to about 80° C. making certain that all ingredients are dissolved. Glycerine is added and then slowly Cellosize is mixed to make Phase A.

The ingredients of Phase B are mixed and heated to 85° C. until all waxes are melted. Phases A and B are mixed, and agitation is continued for 15 minutes. The solution is cooled to about 35° C., perfume is added, and the final product is cooled to about 25° C.

A soft, smooth feeling and pleasing sheen are imparted to skin treated with the lotion.

EXAMPLE 16

Floating Bath Oil

| | Parts |
|---|---|
| Solulan PB-20 (ethoxylated lanolin) | 1.00 |
| Oleyl alcohol | 5.00 |
| Acetulan (acetylated lanolin) | 10.00 |
| Light mineral oil | 47.50 |
| Isopropyl palmitate | 28.00 |
| Dimethyllaurylamine oleate | 3.50 |
| Perfume | 5.00 |
| TOTAL | 100.00 |

All of the ingredients except perfume are blended to homogeneity. Perfume is then added and the solution mixed until uniform.

After use of the bath oil, the skin feels clean and soft to the touch.

EXAMPLE 17

Suntan Oil

| | Parts |
|---|---|
| Light mineral oil | 54.60 |
| 2-Ethylhexyl palmitate | 33.50 |
| Lauryl myristate | 5.00 |
| Escalol 507 (p-dimethylaminoamyl benzoate) | 1.90 |
| Dimethyllaurylamine oleate | 3.50 |
| Perfume | 1.50 |
| TOTAL | 100.00 |

All of the ingredients except perfume are blended to homogeneity. Perfume is added and mixing is continued until a uniform product results.

When spread over the skin, the formulation provides a smooth, protective film effective in screening the sun's rays and moisturizing the skin.

EXAMPLE 18

Instant Hair Conditioner

| | Parts |
|---|---|
| Phase A | |
| Glycerine | 5.00 |
| EMCOL E-607S (Quaternium 7, Witco Chemical Co., Inc., Los Angeles, Ca.; antistatic agent) | 0.50 |
| Water | 81.50 |
| Phase B | |
| Glycerol monostearate | 4.00 |

| | Parts |
|---|---|
| Cetyl alcohol | 0.75 |
| Stearyl alcohol | 0.75 |
| Lanolin | 1.00 |
| Polyethylene glycol 400 monooleate | 5.00 |
| Dimethyllaurylamine oleate | 1.00 |
| Phase C | |
| Perfume | 0.20 |
| Sodium benzoate | 0.10 |
| Color | 0.20 |
| TOTAL | 100.00 |

All of the ingredients of Phase A are mixed and heated to 80° C. and in a separate vessel all of Phase B ingredients are mixed and heated to 80° C. These solutions are then mixed together with agitation and cooled to 45° C. whereupon color, perfume and sodium benzoate are added. The preparation is then allowed to cool to room temperature.

The use of this preparation on hair results in soft lustrous hair.

In Examples 19–26 the term "dimethyl lauryl amine oleate" is utilized to refer to the product obtained by reacting oleic acid with dimethyl lauryl amine in a ratio of about 1.25:1, in a manner similar to Example 1.

EXAMPLE 19

Hair Conditioning Rinse

A useful hair conditioning rinse is as follows:

| | Parts |
|---|---|
| Dimethyllaurylamine oleate | 2.0% |
| Polyethylene glycol 6000 distearate | 4.0% |
| Glycerin | 3.0% |
| Formaldehyde | 0.1% |
| Deionized water q.s. | 100 |

EXAMPLE 20

Hair Shampoo

A useful hair shampoo is as follows:

| | Parts |
|---|---|
| Sodium lauryl polyoxyethyleneglycol sulfate (30%) | 30.0% |
| Sodium lauryl sulfate (30%) | 10.0% |
| Dimethyllaurylamine oleate | 2.0% |
| Ethyleneglycol monostearate | 2.0% |
| Sodium chloride | 0.5% |
| Citric acid | 0.5% |
| Formaldehyde | 0.1% |
| Diethanollauramide | 5.0% |
| Deionized water q.s. | 100 |

EXAMPLE 21

Hand/Body Lotion

A useful hand/body lotion is as follows:

| | Parts |
|---|---|
| Mineral oil, light 70/80 | 15.0% |
| Sorbitan oleate | 5.5% |
| Stearyl alcohol | 2.5% |
| Dimethyllaurylamine oleate | 2.0% |
| Polyethyleneglycol 2000 monostearate (PEG 40 stearate) | 4.5% |
| Methyl paraben | 0.1% |
| Propyl paraben | 0.04% |
| Deionized water q.s. | 100 |

EXAMPLE 22

Hand Creme

A useful hand creme is as follows:

| | Parts |
|---|---|
| Mineral oil light 70/80 | 15.0% |
| Sorbitan oleate | 5.5% |
| Stearyl alcohol | 8.0% |
| Cetyl alcohol | 2.0% |
| Dimethyllaurylamine oleate | 2.0% |
| Polyethyleneglycol 2000 monostearate (PEG 40 stearate) | 4.5% |
| Methyl paraben | 0.1% |
| Propyl paraben | 0.04% |
| Deionized water q.s. | 100 |

EXAMPLE 23

Soap Bars

Soap pellets are made by adding a slight excess of 50% caustic over stoichiometry to a 17:3 ratio of distilled tallow and coconut oil fatty acids. The mass is then dried and pelletized. The pellets contain approximately 12% moisture.

Soap Bar Formulation:

| | Gold Bar | Pink Bar |
|---|---|---|
| Tallow/coco soap/pellets | 9000 g | 9000 g |
| Slurry | 250 g | 282 g |
| Perfume | 0.8 g | 0.8 g |
| Dimethyllaurylamine oleate | — | 191.2 |

(slurry consists of water, pigments and bacteriostat)

The slurry, perfume, then other additives are added separately to the soap pellets while mixing thoroughly. This mixture is then passed through a three roll mill, then an extruder. This is repeated two or three times for thorough mixing and homogeneity. The extruded soap is then cut into size and formed.

50 bars of each of the gold and pink type were evaluated by 43 panelists and the results are as follows:

| | | Pink | Gold | Equal |
|---|---|---|---|---|
| 1. | How easily it lathers | 48.8 | 23.2 | 28.0 |
| 2. | How easily the lather rinses | 25.6 | 18.6 | 55.8 |
| 3. | Skin feel after towel drying (softness) | 44.8 | 20.9 | 34.9 |
| 4. | Skin feel (smoothness) | 32.6 | 16.3 | 51.1 |
| 5. | Over-all performance | 37.2 | 25.6 | 37.2 |

The above results indicate a preference for the pink bar containing dimethyl lauryl amine oleate over the gold bar in the over-all performance as well as skin feel after drying and the quality of lather during bathing.

EXAMPLE 24

Dishwashing Liquid

A laboratory-made dishwashing liquid was comprised of the following formulation:

|  | % by weight |
| --- | --- |
| Sodium dodecylbenzene sulfonate 60% | 26.2 |
| Sodium xylene sulfonate 60% | 1.3 |
| $C_8$–$C_{12}$ linear alcohol ethoxylate (3–5 moles) | 10.0 |
| Triethanolamine laurylsulfate 60% | 10.0 |
| Coconutalkyldiethanolamide (superamide) | 4.0 |
| Dimethylcoconutalkylamine oxide 50% | 2.7 |
| Deionized water | to 100.0 |

One-half of the formula was evaluated without modification (Formula B) and the other half was evaluated after having 2 percent, by weight, of dimethyllaurylamine oleate added thereto (Formula A). Fifteen panelists responded with the following results:

|  | Formula A | Formula B | Equal |
| --- | --- | --- | --- |
| 1. Hand feel after towel drying (softness) | 6 | 5 | 4 |
| 2. Hand feel after towel drying (smoothness) | 7 | 3 | 5 |
| 3. Dish Cleaning | 6 | 4 | 5 |
| 4. Overall perference | 5 | 5 | 5 |

The above results indicate a preference for Formula A in hand feel and dish cleaning.

EXAMPLE 25

Dishwashing Liquid

Using commercially available dishwashing liquid "Joy" and Joy plus 2%, by weight, of dimethyl lauryl amine oleate on artificially soiled 9" plates (the artificial soil consisted of 5 grams of a mixture containing 65% beef tallow, 8.7% oleic acid and 26.3% mineral oil placed on each plate), the plates were stacked and washed individually.

| Product A | (Joy) washed 9½ dishes in run #1 and 9 dishes in run #2 |
| --- | --- |
| Product B | (Joy and dimethyl lauryl amine oleate) washed 11 dishes in run #1 and 11 dishes in run #2 |

The washing was discontinued when a greasy feel was detected on the dishes after rinsing.

The results show that the dimethyl lauryl amine oleate improved the dishwashing performance of commercially available dishwashing liquid.

EXAMPLE 26

Hand Lotion

A hand lotion was prepared in accordance with the following formulation:

| Dimethyllaurylamine oleate | 2% by weight |
| --- | --- |
| Polyethyleneglycol 6000 distearate | 6% |
| Ethyl alcohol | 5% |
| Glycerin | 5% |
| Distilled water | 82% |

The product was compared to a control consisting of all the constituents listed above, except the dimethyllaurylamine oleate was omitted and an additional 2% water employed.

Two trained assessors evaluated the degree of hand dryness and flaking. Two lotions were employed; Lotion A represented the control and Lotion B the product containing the dimethyllaurylamine oleate. The products were dispensed in 30 ml. amber glass dropper bottles, appropriately labeled. The 25 panelists were instructed to use the product as freely as desired both in frequency and quantity in the same manner than they would use any commercial hand lotion. The panelist was informed to use Lotion A, firstly for one week. The panelist would report at 8 A.M. for an evaluation, taking care not to use any lotion the morning of the evaluation. This was necessary to prevent masking by heavy applications of lotion prior to examination. Also, occasionally the polyethyleneglycol ester would crystallize or powder giving a potential for misinterpretation as flakiness if readings were made, under magnification, within several hours of an application.

Panelists started with application day 1 on Sunday and examination day 1 on the following day. The panelist was examined and evaluated each morning Monday through Friday. On the following Sunday, the panelist initiated the use of Lotion B and the panelist examined over the next two weeks Monday through Friday.

The method of evaluating skin dryness is a modification of the methods reported in J. Soc. Cosmet. Chem. 25, 519 (1974) and IBID, 24, 31 (1973). It consists of the use of a simple numerical scoring system to assess six areas of the hand according to the following scheme:

0 = no visible signs of dryness
1 = slight dryness
2 = marked dryness and/or slight flaking
3 = severe dryness and/or marked flaking
4 = severe flaking and/or slight fissures
6 = severe fissures The areas of the hand assessed were: back of hand, thumb web, other webs, front of fingers, back of fingers. The twelve areas (6 on each hand) were summed to give a total score. Panelists were initially selected on the basis of an evaluation of widespread severe dryness, severe flaking or/and fissuring.

After the end of the trial, results were examined for statistically significant differences between A and B lotions. Because the trial was initiated with "initial" hand scores (untreated), it was possible to calculate mean changes from the previous hand scores. These changes were calculated and used as data for the analysis of variance. The results for each assessor were calculated separately and then combined to give an overall mean.

The results were as follows:

|  | Mean Total Hand Scores |
| --- | --- |
| Lotion A | 14.6 |
| Lotion B | 11.9 |
| Initial pre-test | 14.8 |

Lotion A produced no significant differences from the initial evaluation or pre-test conditions, while B demonstrated a moderately but significant change from both pre-test and Lotion A mean values.

EXAMPLE 27

Evaluation of Skin Irritation

A solution, in propylene glycol, USP, of one percent, by weight, of the product obtained by reacting oleic acid with dimethyllaurylamine in a ratio of about 1.25:1 in a manner similar to Example 1, was evaluated for skin irritation. The method employed was that described in the Hazardous Substances Labeling Act Regulations, Code of Federal Regulations 16, Part 1500.41, U.S.A. A doseage of 0.5 ml per patch with four patches per rabbit tration of 5 weight percent, the solution is still considered to be only a moderate skin irritant. The raw data are as follows:

|  | Exposure Time Hours | Exposure Unit Value Rabbit 1 | Exposure Unit Value Rabbit 2 | Exposure Unit Value Rabbit 3 | Exposure Unit Value Rabbit 4 | Exposure Unit Value Rabbit 5 | Exposure Unit Value Rabbit 6 |
|---|---|---|---|---|---|---|---|
| Erythema and eschar formation |  |  |  |  |  |  |  |
| Intact skin | 24 | 2 | 2 | 3 | 3 | 3 | 2 |
| " | 72 | 2 | 2 | 2 | 2 | 2 | 2 |
| Abraded skin | 24 | 3 | 3 | 3 | 3 | 3 | 3 |
| " | 72 | 3 | 3 | 3 | 3 | 3 | 3 |
| Subtotal |  | 10 | 10 | 11 | 11 | 11 | 10 |
| Edema formation |  |  |  |  |  |  |  |
| Intact skin | 24 | 2 | 2 | 3 | 3 | 2 | 2 |
| " | 72 | 2 | 2 | 2 | 2 | 2 | 2 |
| Abraded skin | 24 | 3 | 3 | 3 | 3 | 3 | 3 |
| " | 72 | 3 | 3 | 3 | 3 | 3 | 3 |
| Subtotal |  | 10 | 10 | 11 | 11 | 10 | 10 |
| TOTAL |  | 20 | 20 | 22 | 22 | 21 | 20 |
| AVERAGE |  | 5 | 5 | 5.2 | 5.2 | 5.1 | 5 | was utilized, on each of six rabbits. The skin irritation index was determined to be 0.0. The raw data are as follows:

|  | Exposure Time Hours | Exposure Unit Value Rabbit 1 | Exposure Unit Value Rabbit 2 | Exposure Unit Value Rabbit 3 | Exposure Unit Value Rabbit 4 | Exposure Unit Value Rabbit 5 | Exposure Unit Value Rabbit 6 |
|---|---|---|---|---|---|---|---|
| Erythema and eschar formation |  |  |  |  |  |  |  |
| Intact skin | 24 | 0 | 0 | 0 | 0 | 0 | 0 |
| " | 72 | 0 | 0 | 0 | 0 | 0 | 0 |
| Abraded skin | 24 | 0 | 0 | 0 | 0 | 0 | 0 |
| " | 72 | 0 | 0 | 0 | 0 | 0 | 0 |
| Subtotal |  | 0 | 0 | 0 | 0 | 0 | 0 |
| Edema formation |  |  |  |  |  |  |  |
| Intact skin | 24 | 0 | 0 | 0 | 0 | 0 | 0 |
| " | 72 | 0 | 0 | 0 | 0 | 0 | 0 |
| Abraded skin | 24 | 0 | 0 | 0 | 0 | 0 | 0 |
| " | 72 | 0 | 0 | 0 | 0 | 0 | 0 |
| Subtotal |  | 0 | 0 | 0 | 0 | 0 | 0 |
| TOTAL AVERAGE |  | 0 | 0 | 0 | 0 | 0 | 0 |

EXAMPLE 28

Evaluation of Skin Irritation

A solution in propylene glycol, USP, of five percent, by weight, of the product obtained by reacting oleic acid with dimethyllaurylamine in a ratio of about 1.25:1 in a manner similar to Example 1, was prepared and evaluated in the same manner as outlined in Example 27. The primary skin irritation index number was determined to be 5.1, showing that at the high active concentration of 5 weight percent, the solution is still considered to be only a moderate skin irritant.

EXAMPLES 29 THROUGH 66

Preparation of Various Products

In the following examples various tertiary amines were reacted with various acids, in a variety of equivalent ratios to yield compositions within the scope of the present invention. The typical preparation procedure is to add the amine to the acid and to heat the mixture to about 130° C. for about 1.5 hours. Subsequently, the reaction mixture is allowed to cool under vacuum to room temperature, the vacuum released and the product removed.

|  | Amines | Equivalent Weight | grams | moles | Acid | Equivalent Weight | grams | moles |
|---|---|---|---|---|---|---|---|---|
| 29. | Dimethyloctadecylamine (Armeen 18D) | 300 | 36 | 0.12 | linoleic (Emersol 315) | 280 | 42 | 0.15 |
| 30. | Dimethyloctadecylamine (Armeen 18D) | 300 | 36 | 0.12 | dimer (Empol 1016) $HO_2C(C_{34}H_{62})CO_2H$ | 290 | 43.5 | 0.15 |
| 31. | Dimethyloctadecylamine (Armeen 18D) | 300 | 39 | 0.13 | isostearic (Emersol 871) | 268 | 43.6 | 0.16 |
| 32. | Dimethyloctadecylamine (Armeen 18D) | 300 | 36 | 0.12 | Westvaco Diacid 1550 $HO_2C(C_{19}H_{34})CO_2H$ | 176 | 53.0 | 0.30 |
| 33. | Dimethyloctylamine (Armeen 8D) | 156 | 23.6 | 0.15 | oleic (Neo-Fat 90-04) | 277 | 51.9 | 0.19 |
| 34. | Dimethyloctylamine (Armeen 8D) | 156 | 23.6 | 0.15 | linoleic (Emersol 315) | 280 | 52.5 | 0.19 |
| 35. | Dimethyloctylamine (Armeen 8D) | 156 | 18.7 | 0.12 | dimer (Empol 1016) | 290 | 43.5 | 0.15 |
| 36. | Dimethyloctylamine (Armeen 8D) | 156 | 21.8 | 0.14 | isostearic (Emersol 871) | 268 | 46.9 | 0.18 |
| 37. | Dimethyloctylamine (Armeen 8D) | 156 | 78.7 | 0.12 | Westvaco Diacid 1550 | 176 | 53.0 | 0.30 |
| 38. | Dimethyloctylamine (Armeen 8D) | 156 | 16.7 | 0.11 | Cocoylalkoxycarboxylic acid | 548 | 54.4 | 0.10 |

-continued

| Amines | Equivalent Weight | grams | moles | Acid | Equivalent Weight | grams | moles |
|---|---|---|---|---|---|---|---|
| 39. N—cocomorpholine (Armeen NCMD) | 283 | 34.0 | 0.12 | oleic (Neo-Fat 90-04) | 277 | 41.6 | 0.15 |
| 40. N—cocomorpholine (Armeen NCMD) | 283 | 34.0 | 0.12 | linoleic (Emersol 315) | 280 | 42.0 | 0.15 |
| 41. N—cocomorpholine (Armeen NCMD) | 283 | 34.0 | 0.12 | dimer (Empol 1016) | 290 | 43.5 | 0.15 |
| 42. N—cocomorpholine (Armeen NCMD) | 283 | 34.0 | 0.12 | isostearic (Emersol 871) | 268 | 40.2 | 0.15 |
| 43. N—cocomorpholine (Armeen NCMD) | 283 | 34.0 | 0.12 | Westvaco Diacid 1550 | 176 | 53.0 | 0.30 |
| 44. Dimethyldodecylamine (Armeen DM12D) | 220 | 44.0 | 2.0 | oleic (Neo-Fat 90-04) | 277 | 69.2 | 2.5 |
| 45. Dimethyldodecylamine (Armeen DM12D) | 220 | 26.4 | 0.12 | linoleic (Emersol 315) | 280 | 42.0 | 0.15 |
| 46. Dimethyldodecylamine (Armeen DM12D) | 220 | 35.2 | 0.16 | dimer (Empol 1016) | 290 | 58.0 | 0.2 |
| 47. Dimethyldodecylamine (Armeen DM12D) | 220 | 30.8 | 0.14 | isostearic (Emersol 871) | 268 | 46.9 | 0.18 |
| 48. Dimethyldodecylamine (Armeen DM12D) | 220 | 26.4 | 0.12 | Westvaco Diacid 1550 | 176 | 53.0 | 0.30 |
| 49. Dimethyldodecylamine (Armeen DM12D) | 220 | 22.0 | 0.10 | cocoylalkoxycarboxylic RO(CH2CH2O)7CH2CO2H | 548 | 54.4 | 0.10 |
| 50. Dimethyldodecylamine (Armeen DM12D) | 220 | 56.0 | 0.25 | distilled coco fatty acids (Neo-Fat 265) | 265 | 67.0 | 0.32 |
| 51. Dimethyldodecylamine (Armeen DM12D) | 220 | 56.0 | 0.25 | triple-pressed stearic (Neo-Fat 18-35) | 267 | 89.0 | 0.33 |
| 52. Dimethyldodecylamine (Armeen DM12D) | 218 | 84.8 | 0.39 | stearoyl sarcosine | 337 | 165 | 0.49 |
| 53. Dimethyldodecylamine (Armeen DM12D) | 218 | 107 | 0.49 | lauroyl sacosine | 240 | 145 | 0.60 |
| 54. Dimethylcoconutalkylamine (Armeen DMCD) | 230 | 27.6 | 0.12 | oleic (Neo-Fat 90-04) | 277 | 41.6 | 0.15 |
| 55. Dimethylcoconutalkylamine (Armeen DMCD) | 230 | 32.9 | 0.14 | linoleic (Emersol 315) | 218 | 49.0 | 0.18 |
| 56. Dimethylcoconutalkylamine (Armeen DMCD) | 230 | 28.2 | 0.12 | dimer (Empol 1016) | 290 | 43.5 | 0.15 |
| 57. Dimethylcoconutalkylamine (Armeen DMCD) | 230 | 29.9 | 0.13 | isostearic (Emersol 871) | 268 | 43.6 | 0.16 |
| 58. Dimethylcoconutalkylamine (Armeen DMCD) | 230 | 27.6 | 0.12 | Westvaco Diacid 1550 | 176 | 53.0 | 0.30 |
| 59. RCONH(CH2)3N(CH3)2 RC = Coco Fatty Acids | 295 | 148 | 0.50 | oleic (Neo-Fat 94-04) | 279 | 200.0 | 0.72 |
| 60. Dimethyl tetradecyl amine (Armeen DM14D) | 245 | 120 | 0.49 | oleic (Neo-Fat 94-04) | 279 | 168 | 0.50 |
| 61. Dimethyl hexadecyl amine (Armeen DM16D) | 273 | 120 | 0.44 | oleic (Neo-Fat 94-04) | 279 | 150 | 0.54 |
| 62. RCONH(CH2)3N(CH3)2 RC = oleic acid | 278 | 150 | 0.54 | oleic (Neo-Fat 94-04) | 279 | 180 | 0.65 |
| 63. Polyoxyethylene (15) tallow amine (Ethomeen T/25) | 925 | 200 | 0.22 | oleic (Neo-Fat 94-04) | 279 | 80 | 0.29 |
| 64. Bis(2-hydroxyethyl) tallow amine | 350 | 167 | 0.48 | oleic (Neo-Fat 94-04) | 279 | 174 | 0.62 |
| 65. Bis(2-hydroxyethyl) tallow amine | 350 | 35 | 0.10 | oleyl sarcosine | 350 | 43.8 | 0.125 |
| 66. N—cocomorpholine | 283 | 28.3 | 0.10 | Westvaco Diacid 1550 | 177 | 22.1 | 0.125 |

EXAMPLES 67 & 68

Preparation

Two moles of α-olefin oxides of the general formula

(equivalent weight 286) were reacted with one mole of N,N-dimethyl-1,3-diaminopropane to yield a product of the formula

having an equivalent weight of 673. One mole of the product was reacted with one mole of oleic acid (Example 67) and one mole of the product was reacted with two moles of oleic acid (Example 68) to yield compositions within the scope of the present invention.

EXAMPLES 69 THROUGH 74

Preparation

Two moles of propylene oxide were reacted with one mole of N,N-dimethyl-1,3-diaminopropane to yield a product of the formula [HOCH(CH3)CH2]2N(CH2)3N(CH3)2. One mole of the product was reacted with one mole of oleic acid (Example 69) and with two moles of oleic acid (Example 70) to yield compositions within the scope of the invention.

In the same manner as above, five moles of propylene oxide were utilized to yield a mixture containing products of the formula:

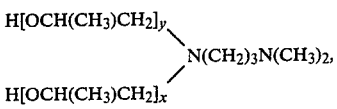

where x+y=5. One mole of the product mixture was reacted with one mole of oleic acid (Example 71) and with two moles of oleic acid (Example 72) to yield compositions within the scope of the invention.

Again, similar to the above procedure, ten moles of propylene oxide were reacted to yield a mixture containing products of the formula:

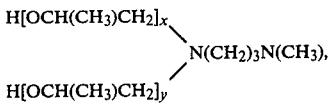

where x+y=10. One mole of the product mixture was reacted with one mole oleic acid (Example 73) and with two moles of oleic acid (Example 74) to yield compositions within the scope of the invention.

Examples 67-74 represent alternative embodiments to the general tertiary amines disclosed hereinbefore. In the embodiment represented by Examples 67 and 68, the tertiary amine utilized in the production of the salt and other product, has the general formula

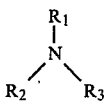

wherein $R_1$ is

$R_5$ representing an aliphatic group containing from about 8 to about 22 carbon atoms and $R_2$ and $R_3$ are $CH_3$—.

In the embodiment represented by Examples 69-73, the tertiary amine utilized in the production of the salt and other products, has the general formula

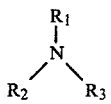

wherein $R_1$ has the formula

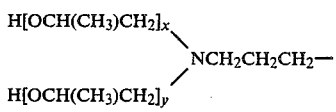

wherein x and y are integers from 1 to 9 and the sum of x and y is from 2 to about 10 and $R_2$ and $R_3$ are $CH_3$—.

In either of the above embodiments, the tertiary amine may be reacted with any of the acids represented by the formula $R_4$—H as defined hereinabove, in any molar ratio of amine:acid from about 0.3:1 to about 3.3:1.

The resulting salts and products may be utilized in the same manner as the other salts and products of this invention, such as, in making skin and hair contacting formulations, dishwashing formulations, and soap bars.

What is claimed is:

1. A process for the lubrication, emolliency, softening and conditioning of skin or hair comprising contacting said skin or hair with an effective amount of a composition comprising a tertiary amine salt of the formula:

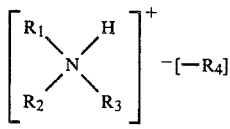

wherein $R_1$ is selected from the group consisting of saturated and unsaturated aliphatic groups containing from about 8 to about 22 carbon atoms,

$RN(CH_3)CH_2CH_2CH_2$—, $RN(CH_2CH_2O)_{1-5}HCH_2CH_2CH_2$—,

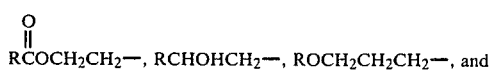

$RCOCH_2CH_2$—, $RCHOHCH_2$—, $ROCH_2CH_2CH_2$—, and

$R_3$ is selected from the group consisting of aliphatic groups containing from one to about two carbon atoms $H[O(CH_3)CHCH_2]_{1-15}$— and $H(OCH_2CH_2)_{1-15}$—, $R_2$ is selected from the group consisting of aliphatic groups containing from about 8 to about 22 carbon atoms,

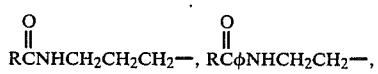

$R(OCH_2CH_2CH_2)_2N(CH_3)CH_2CH_2CH_2$—,
$R(OCH_2CH_2CH_2)_2N(CH_2CH_2O)_{1-5}HCH_2CH_2CH_2$—,

$CH_3O[CH_2CH(CH_3)O]_{1-5}CH_2CH_2CH_2$—, $H[O(CH_3)CHCH_2]_{3-8}$—, $H[O(CH_3)CHCH_2]_{3-8}OCH_2CH_2$—, $RCHOHCH_2$—, $ROCH_2CH_2CH_2$—, aliphatic groups containing from one to about two carbon atoms and $H[O(CH_3)CHCH_2]_{1-15}$—, $H(OCH_2CH_2)_{1-15}$—, and $R_4$ is selected from the group consisting of

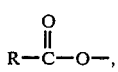

$RCH=CH_2SO_3$—, $RCONHCH(CH_3)CO_2$—, $ROSO_3$—, $RC_6H_5SO_3$—, $RO[CH_2CH_2O]_{1-10}CH_2CO_2$—, $RNHCOCH=CHCO_2$—, isostearic acid radical, ricinoleic acid radical, hydroxystearic acid radical, phenylstearic acid radical, and radicals of dibasic acids containing from about 6 to about 36 carbon atoms, wherein in all instances R represents a saturated and unsaturated aliphatic group containing from about 8 to about 18 carbon atoms, z is 0 or 1.

2. The process of claim 1 wherein $R_1$ is a saturated or unsaturated aliphatic group containing from about 8 to about 22 carbon atoms, $R_2$ and $R_3$ are selected from the group consisting of methyl, ethyl $H[O(CH_3)CHCH_2]_{1-15}$— and $H(OCH_2CH_2)_{1-15}$—, and $R_4$ is a saturated or unsaturated aliphatic carboxylic acid containing from about 8 to about 22 carbon atoms.

3. A process for the lubrication, emolliency, softening and conditioning of skin or hair comprising contacting said skin or hair with a composition comprising a tertiary amine salt selected from the group consisting of dimethyllaurylamine oleate, dimethyllaurylamine stearate, dimethylpalmitylamine oleate, diethyllaurylamine oleate, dimethylpalmitylamine stearate, polyoxyethylene(15) tallowamine oleate, N,N-dimethylcocoamine isostearate, and N,N-dimethyloctadecylamine oleate.

4. The process of claim 1, 2, or 3 wherein said composition comprises from about 0.1 to about 2.0 percent, by weight, based on the total weight of the composition of said tertiary amine salt.

5. A process for the lubrication, emolliency, softening and conditioning of skin or hair comprising contacting said skin or hair with a composition comprising from about 0.1 to about 5.0 percent, by weight, based on the total weight of the composition, of a tertiary amine salt of a product made by the process of reacting a tertiary amine of the formula:

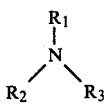

and an acid of the formula:

wherein $R_1$, $R_2$, $R_3$, and $R_4$ have the meanings defined in claim 1, in a molar ratio of amine:acid from about 0.3:1 to about 3.3:1.

6. The process of claim 5 wherein said product is made by the process wherein $R_1$ is a saturated or unsaturated aliphatic group containing from about 8 to about 22 carbon atoms, $R_2$ and $R_3$ are selected from the group consisting of methyl, ethyl $H[O(CH_3)CHCH_2]_{1-15}-$ and $H(OCH_2CH_2)_{1-15}-$, and $R_4$ is a saturated or unsaturated aliphatic carboxylic acid containing from about 8 to about 22 carbon atoms.

7. The process of claim 5 wherein said product is made by the process wherein the tertiary amine is selected from the group consisting of dimethyllaurylamine, dimethylpalmitylamine, diethyllaurylamine, polyoxyethylene(15)tallowamine, N,N-dimethylcocoamine and N,N-dimethyloctadecylamine and the acid is selected from the group consisting of oleic acid, stearic acid, and isostearic acid.

8. A process for the lubrication, emolliency, softening and conditioning of skin or hair comprising contacting said skin or hair with a composition comprising from about 0.1 to about 5.0 percent, by weight, based on the total weight of the composition of a tertiary amine salt of a product made by the process of mixing water, or tertiary amine of the formula

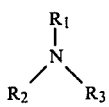

and an acid of the formula:

wherein $R_1$, $R_2$, $R_3$, and $R_4$ have the meanings defined in claim 1, in a molar ratio of amine:acid from about 0.3:1 to about 3.3:1.

9. The process of claim 8 wherein said product is made by the process wherein $R_1$ is a saturated or unsaturated aliphatic group containing from about 8 to about 22 carbon atoms, $R_2$ and $R_3$ are selected from the group consisting of methyl, ethyl, $H[O(CH_3)CHCH_2]_{1-15}-$ and $H(OCH_2CH_2)_{1-15}-$, and $R_4-H$ is a saturated or unsaturated aliphatic carboxylic acid containing from about 8 to about 22 carbon atoms.

10. The process of claim 8 wherein said product is made by the process wherein the tertiary amine is selected from the group consisting of dimethyllaurylamine, dimethylpalmitylamine, diethyllaurylamine, polyoxyethylene(15)tallowamine, N,N-dimethylcocoamine and N,N-dimethyl-octadecylamine and the acid is selected from the group consisting of oleic acid, stearic acid, and isostearic acid.

11. A process for the lubrication, emolliency, softening and conditioning of skin or hair comprising contacting said skin or hair with a composition comprising from about 0.1 to about 5.0 percent, by weight, based on the total weight of the composition, of a tertiary amine salt of the formula

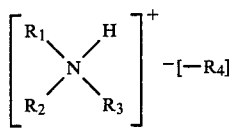

wherein $R_1$ is

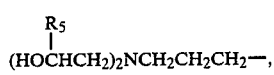

$R_5$ representing an aliphatic group containing from about 8 to about 22 carbon atoms, $R_2$ and $R_3$ and $CH_3-$, and $R_4$ is as defined in claim 1.

12. A process for the lubrication, emolliency, softening and conditioning of skin or hair comprising contacting said skin or hair with a composition comprising from about 0.1 to about 5.0 percent, by weight, based on the total weight of the composition, of a product prepared by the process of reacting a tertiary amine of the formula

with an acid of the formula:

in a molar ratio of amine:acid from about 0.3:1 to about 3.3:1, wherein $R_1$, $R_2$, $R_3$, and $R_4$ are as defined in claim 11, or of a product prepared by the process of reacting water, a tertiary amine of the formula

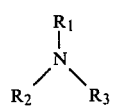

with an acid of the formula:

in a molar ratio of amine:acid from about 0.3:1 to about 3.3:1, wherein $R_1$, $R_2$, $R_3$ and $R_4$ are as defined in claim 11.

* * * * *